(12) United States Patent
Martinez et al.

(10) Patent No.: US 6,709,645 B1
(45) Date of Patent: Mar. 23, 2004

(54) SYNTHESIS OF LABELED METABOLITES

(75) Inventors: Rodolfo A. Martinez, Santa Fe, NM (US); Louis A. Silks, III, Los Alamos, NM (US); Clifford J. Unkefer, Los Alamos, NM (US); Robert Atcher, White Rock, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/419,310

(22) Filed: Apr. 18, 2003

(51) Int. Cl.[7] .................. A61K 51/04; C07C 317/00; C07C 321/00; C07C 43/00
(52) U.S. Cl. .................. 424/1.81; 568/27; 568/28; 568/32; 568/579; 568/606; 568/613; 568/671
(58) Field of Search .................. 568/27, 28, 30, 568/32, 36, 38, 39, 55, 579, 606, 613, 671; 424/1.68, 1.81

(56) References Cited

PUBLICATIONS

CHEMCATS AN:2001:210268 Synthelec Product list on–line Oct. 12, 2001.*
CA:115:249703 abs of Journal of Chromatography by Black et al 558(2) pp 393–404 1991.*
CA:116:83169 abs of Journal of Labelled Compounds and Radiopharm. by Harrison, J. M. 29(1) pp 1175–80 1991.*
CA:101:109832 abs of Helvetica Chim. Acta by Gabriel et al 67(4) pp 1070–82 1984.*
CA:87:133486 abs of Chemische Berichte by Schlecker et al 110(8) pp 2880–904 1977.*
CA:89:128652 abs of Organic Mass Spectrometry by Broer et al 13(4) pp 232–5 1978.*
CA:115:249703 abs of J. of Chromatography by Black et al 558(2) pp 393–404 1991.*

* cited by examiner

Primary Examiner—Jean F. Vollano
(74) Attorney, Agent, or Firm—Bruce H. Cottrell

(57) ABSTRACT

The present invention is directed to labeled compounds, for example, isotopically enriched mustard gas metabolites including: $[1,1',2,2'-{}^{13}C_4]$ethane, $1,1'$-sulfonylbis[2-(methylthio); $[1,1',2,2'-{}^{13}C_4]$ethane, 1-[[2-(methylsulfinyl)ethyl]sulfonyl]-2-(methylthio); $[1,1',2,2'-{}^{13}C_4]$ethane, $1,1'$-sulfonylbis[2-(methylsulfinyl)]; and, $2,2'$-sulfinylbis([1,2-${}^{13}C_2$]ethanol of the general formula

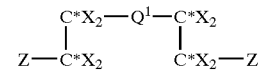

where $Q^1$ is selected from the group consisting of sulfide (—S—), sulfone (—S(O)—), sulfoxide (—S(O$_2$)—) and oxide (—O—), at least one C* is ${}^{13}$C, X is selected from the group consisting of hydrogen and deuterium, and Z is selected from the group consisting of hydroxide (—OH), and —Q$^2$—R where Q$^2$ is selected from the group consisting of sulfide (—S—), sulfone(—S(O)—), sulfoxide (—S(O$_2$)—) and oxide (—O—), and R is selected from the group consisting of hydrogen, a $C_1$ to $C_4$ lower alkyl, and amino acid moieties, with the proviso that when Z is a hydroxide and Q$^1$ is a sulfide, then at least one X is deuterium.

10 Claims, No Drawings

SYNTHESIS OF LABELED METABOLITES

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to isotopically enriched mustard gas metabolites labeled with carbon-13 or with carbon-13 and hydrogen-2.

BACKGROUND OF THE INVENTION

Several mass spectral screening procedures have been developed for the detection and identification of metabolic products resulting from exposure to chemical warfare (CW) agents (e.g., vesicants such as mustard gas and other mustard agents, nerve agents such as the organic esters of substituted phosphoric acid including tabun, sarin and the like, and incapacitants such as BZ (3-quinuclidinyl benzilate)). In order to positively identify the suspected metabolites, an isotopically enriched sample of the metabolite must be available. The amount, or in some cases the presence, of the suspected metabolite is derived by isotope dilution (ID) mass spectrometry. Isotope dilution mass spectrometry is based on the addition of isotopically enriched sample to the unknown samples. The equilibration of the samples, including both the isotopically labeled material and the unknown material) alters the isotope ratio that would normally be measured for the native sample alone. This ratio can then be used to establish the presence of a suspected metabolite which can then indicate which CW agent is present.

2,2'-dichloroethyl sulfide, commonly referred to as mustard gas or mustard, was first used by the Germans during World War I. It is a heavy, oily liquid and is nearly colorless and odorless when pure. Other compounds such as $(ClCH_2CH_2)_2NEt$, $(ClCH_2CH_2)_2NMe$ and $(ClCH_2CH_2)_3N$ also fall within the class of compounds known and used as mustard gases. Even today, with the availability of more advanced chemical technologies, mustard gas may still be the war gas of choice due largely to its ease of manufacture.

It is an object of the present invention to provide isotopically enriched mustard gas metabolites.

SUMMARY OF THE INVENTION

In accordance with the purposes of the present invention, as embodied and broadly described herein, the present invention provides labeled compounds of the formula

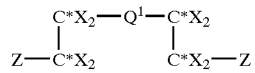

where $Q^1$ is sulfide (—S—), sulfone (—S(O)—), sulfoxide (—S(O$_2$)—) or oxide (—O—), at least one C* is a carbon-13, i.e., $^{13}$C, X is a hydrogen (H) or deuterium (D), and Z is hydroxide (—OH), or —Q$^2$—R where Q$^2$ is sulfide (—S—), sulfone(—S(O)—), sulfoxide (—S(O$_2$)—) or oxide (—O—), and R is hydrogen, a $C_1$ to $C_4$ lower alkyl such as methyl, ethyl, propyl, isopropyl, butyl, isobutyl and t-butyl, or an amino acid moiety, with the proviso that where Z is a hydroxide and Q$^1$ is a sulfide then at least one X is deuterium. Preferably, each C* is a carbon-13, i.e., $^{13}$C. In specific embodiments, the labeled compounds include [1,1',2,2'-$^{13}C_4$]ethane, 1,1'-sulfonylbis[2-(methylthio); [1,1',2,2'-$^{13}C_4$]ethane, 1-[[2-(methylsulfinyl)ethyl]sulfonyl]-2-(methylthio); [1,1',2,2'-$^{13}C_4$]ethane, 1,1'-sulfonylbis[2-(methylsulfinyl)]; and, 2,2'-sulfinylbis([1,2-$^{13}C_2$]ethanol.

The present invention further provides processes of preparing labeled compounds of the formula

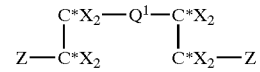

where $Q^1$ is sulfide (—S—), sulfone (—S(O)—), sulfoxide (—S(O$_2$)—) or oxide (—O—), at least one C* is a carbon-13, i.e., $^{13}$C, X is a hydrogen (H) or deuterium (D), and Z is hydroxide (—OH), or —Q$^2$—R where Q$^2$ is sulfide (—S—), sulfone(—S(O)—), sulfoxide (—S(O$_2$)—) or oxide (—O—), and R is a hydrogen, $C_1$ to $C_4$ lower alkyl such as methyl, ethyl, propyl, isopropyl, butyl, isobutyl and t-butyl, or an amino acid moiety. In specific embodiments those labeled compounds include [1,1',2,2'-$^{13}C_4$]ethane, 1,1'-sulfonylbis[2-(methylthio); [1,1',2,2'-$^{13}C_4$]ethane, 1-[[2-(methylsulfinyl)ethyl]sulfonyl]-2-(methylthio); [1,1',2,2'-$^{13}C_4$]ethane, 1,1'-sulfonylbis[2-(methylsulfinyl)]; and, 2,2'-sulfinylbis([1,2-$^{13}C_2$]ethanol.

DETAILED DESCRIPTION

The present invention is concerned with isotopically enriched mustard gas metabolites labeled with carbon-13. By "isotopically enriched" is meant that the common naturally occurring isotope of one or more element have been deliberately enriched with a less common isotope of the same element, e.g., carbon-12 ($^{12}$C) can be replaced with carbon-13 ($^{13}$C) or hydrogen ($^1$H) can be replaced by deuterium ($^2$H). Particularly, the present invention is concerned with labeled compounds of the formula

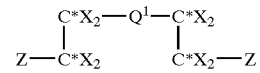

where $Q^1$ is sulfide (—S—), sulfone (—S(O)—), sulfoxide (—S(O$_2$)—) or oxide (—O—), at least one C* is a carbon-13, i.e., $^{13}$C, X is a hydrogen (H) or deuterium (D), and Z is hydroxide (—OH), or —Q$^2$—R where Q$^2$ is sulfide (—S—), sulfone(—S(O)—), sulfoxide (—S(O$^2$)—) or oxide (—O—), and R is hydrogen, a $C_1$ to $C_4$ lower alkyl such as methyl, ethyl, propyl, isopropyl, butyl, isobutyl and t-butyl, or an amino acid moiety, with the proviso that when Z is a hydroxide and Q$^1$ is a sulfide then at least one X is deuterium. Preferably, each C* is a carbon-13, i.e., $^{13}$C.

By the term "amino acid moiety" is meant to portions of, e.g., cysteine or serine such as —CH$_2$CH(NH$_2$)COOH. These may be added through the sulfur (for cysteine) or through the oxygen (for serine).

Among particular isotopically enriched mustard gas metabolites are included: [1,1',2,2'-$^{13}C_4$]ethane, 1,1'-sulfonylbis[2-(methylthio); [1,1',2,2'-$^{13}C_4$]ethane, 1-[[2-(methylsulfinyl)ethyl]sulfonyl]-2-(methylthio); [1,1',2,2'-$^{13}C_4$]ethane, 1,1'-sulfonylbis[2-(methylsulfinyl)]; and, 2,2'-sulfinylbis([1,2-$^{13}C_2$]ethanol.

Each of these labeled metabolites can be synthesized from the same common intermediate, namely, ethyl [1,2-$^{13}C_2$] bromoacetate although other starting materials may be employed. In a process of the present invention, two equivalents of an alkyl bromoacetate such as ethyl $[1,2\text{-}^{13}C_2]$ bromoacetate can be reacted with one equivalent of sodium sulfide ($Na_2S$) in ethanol to form an intermediate addition product (I). The intermediate product can then be reacted with lithium aluminum hydride (LAH) or lithium aluminum deuteride (LAD) in THF depending upon whether a deuterium label is desired on the outermost carbons in relation to the central sulfur atom. Alternatively, a bromoacetaldehyde may be hydrogenated or deuterated to place a deuterium label and after a similar subsequent reaction with sodium sulfide, the innermost carbons in relation to the central sulfur atom may contain a deuterium label. In yet another alternative, deuterium labeling may be carried out at all the carbon sites by both of these processes.

Following hydrogenation or deuteration of the intermediate product (I), the resultant material can be reacted hydrogen peroxide in ethanol to form 2,2'-sulfinylbis($[1,2\text{-}13C_2]$ethanol or deuterated products thereof.

Alternatively, following hydrogenation or deuteration of the intermediate product (I), the resultant material can be reacted with tosyl chloride (TsCl) in, e.g., 90 percent dichloromethane/10 percent pyridine to form a next intermediate product (II).

This next intermediate product (II) can be be reacted with Oxone® in a biphasic mixture of dichlromethane and water followed by reaction with sodium methyl sulfide ($NaSCH_3$) in ethanol to form, e.g., $[1,1',2,2'\text{-}^{13}C_4]$ethane, 1,1'-sulfonylbis[2-(methylthio) or deuterated products thereof.

Reaction of $[1,1',2,2'\text{-}^{13}C_4]$ethane, 1,1'-sulfonylbis[2-(methylthio) or deuterated products thereof with hydrogen peroxide in ethanol can then form a mixture of $[1,1',2,2'\text{-}^{13}C_4]$ethane, 1-[[2-(methylsulfinyl)ethyl]sulfonyl]-2-(methylthio) and $[1,1',2,2'\text{-}^{13}C_4]$ethane, 1,1'-sulfonylbis[2-(methylsulfinyl)] or deuterated products thereof. This mixture can be separated by chromatography.

If desired, additional labeling of oxygen or sulfur atoms may be carried out as well. For example, the compounds can be enriched with oxygen-17 ($^{17}O$) or oxygen-18 ($^{18}O$) or can be enriched with sulfur-33 ($^{33}S$), sulfur-34 ($^{34}S$) or sulfur-36 ($^{36}S$).

The present invention is more particularly described in the following examples which are intended as illustrative only, since numerous modifications and variations will be apparent to those skilled in the art.

EXAMPLE 1

Preparation of 2,2'-sulfinylbis($[1,2\text{-}^{13}C_2]$ethanol was as follows. Two equivalents of ethyl $[1,2\text{-}^{13}C_2]$ bromoacetate was reacted with one equivalent of sodium sulfide ($Na_2S$) to form intermediate product. This intermediate product was then reacted with lithium aluminum hydride (LAH) to form a second intermediate product. This second intermediate product was then reacted with 30 percent hydrogen peroxide in ethanol to form 2,2'-sulfinylbis($[1,2\text{-}^{13}C_2]$ethanol.

EXAMPLE 2

Preparation of $[1,1',2,2'\text{-}^{13}C_4]$ethane, 1,1'-sulfonylbis[2-(methylthio) was as follows. The second intermediate product from example 1 was reacted with tosyl chloride (TsCl) in a mixture of dichloromethane and pyridine to form a third intermediate product. This third intermediate product was then reacted with Oxone® (potassium peroxymonosulfate) in a biphasic mixture of dichlromethane and water followed by sodium methyl sulfide ($NaSCH_3$) in ethanol to form $[1,1',2,2'\text{-}^{13}C_4]$ethane, 1,1'-sulfonylbis[2-(methylthio).

EXAMPLE 3

Preparation of $[1,1',2,2'\text{-}^{13}C_4]$ethane, 1-[[2-(methylsulfinyl)ethyl]sulfonyl]-2-(methylthio) and $[1,1',2,2'\text{-}^{13}C_4]$ethane, 1,1'-sulfonylbis[2-(methylsulfinyl)] were as follows. The $[1,1',2,2'\text{-}^{13}C_4]$ethane, 1,1'-sulfonylbis[2-(methylthio) product from example 2 was reacted with hydrogen peroxide in ethanol to form a mixture of $[1,1',2,2'\text{-}^{13}C_4]$ethane, 1-[[2-(methylsulfinyl)ethyl]sulfonyl]-2-(methylthio) and $[1,1',2,2'\text{-}^{13}C_4]$ethane, 1,1'-sulfonylbis[2-(methylsulfinyl)]. This mixture was then separated by chromatography.

Although the present invention has been described with reference to specific details, it is not intended that such details should be regarded as limitations upon the scope of the invention, except as and to the extent that they are included in the accompanying claims.

What is claimed is:

1. A labeled compound of the formula

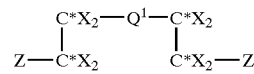

where $Q^1$ is selected from the group consisting of sulfide (—S—), sulfone (—S(O)—), sulfoxide (—S(O$_2$)—) and oxide (—O—), at least one C* is $^{13}C$, X is selected from the group consisting of hydrogen and deuterium, and Z is selected from the group consisting of hydroxide (—OH), and —Q$^2$—R where Q$^2$ is selected from the group consisting of sulfide (—S—), sulfone(—S(O)—), sulfoxide (—S(O$_2$)—) and oxide (—O—), and R is selected from the group consisting of hydrogen, a $C_1$ to $C_4$ lower alkyl, and amino acid moieties, with the proviso that when Z is a hydroxide and Q$^1$ is a sulfide, then at least one X is deuterium.

2. The labeled compound of claim 1 wherein each C* is $^{13}C$.

3. The labeled compound of claim 1 wherein Q$^1$ is a sulfone (—S(O)—).

4. The labeled compound of claim 3 wherein Z is hydroxide.

5. The labeled compound of claim 1 wherein Q$^1$ is a sulfoxide (—S(O$_2$)—).

6. The labeled compound of claim 5 wherein Z is methyl sulfide.

7. The labeled compound of claim 1 wherein said compound is $[1,1',2,2'\text{-}^{13}C_4]$ethane, 1,1'-sulfonylbis[2-(methylthio).

8. The labeled compound of claim 1 wherein said compound is $[1,1',2,2'\text{-}^{13}C_4]$ethane, 1-[[2-(methylsulfinyl)ethyl]sulfonyl]-2-(methylthio).

9. The labeled compound of claim 1 wherein said compound is $[1,1',2,2'\text{-}^{13}C_4]$ethane, 1,1'-sulfonylbis[2-(methylsulfinyl)].

10. The labeled compound of claim 1 wherein said compound is 2,2'-sulfinylbis($[1,2\text{-}^{13}C_2]$ethanol.

* * * * *